(12) United States Patent
Blei et al.

(10) Patent No.: US 8,754,026 B2
(45) Date of Patent: Jun. 17, 2014

(54) PROCESS FOR PRODUCING GRANULES COMPRISING ONE OR MORE COMPLEXING AGENT SALTS

(75) Inventors: Stefan Blei, Mannheim (DE); Michael Schoenherr, Frankenthal (DE); Franz Weber, Eppelheim (DE); Francois Becker, Burrweiler (DE)

(73) Assignee: BASF SE, Ludwigshafen (DE)

( * ) Notice: Subject to any disclaimer, the term of this patent is extended or adjusted under 35 U.S.C. 154(b) by 9 days.

(21) Appl. No.: 13/242,540

(22) Filed: Sep. 23, 2011

(65) Prior Publication Data

US 2012/0077727 A1 Mar. 29, 2012

Related U.S. Application Data

(60) Provisional application No. 61/386,590, filed on Sep. 27, 2010.

(51) Int. Cl.
*C11D 11/00* (2006.01)
*C11D 3/33* (2006.01)
*C11D 7/32* (2006.01)

(52) U.S. Cl.
USPC .......... 510/457; 510/480; 264/12; 23/313 FB

(58) Field of Classification Search
USPC ................. 510/480, 457; 264/12; 23/313 FB
See application file for complete search history.

(56) References Cited

U.S. PATENT DOCUMENTS

| 4,655,780 A * | 4/1987 | Chun et al. ........................ 8/108.1 |
| 5,849,950 A | 12/1998 | Greindl et al. |
| 5,981,798 A | 11/1999 | Schönherr et al. |
| 6,426,229 B1 * | 7/2002 | Yamamoto et al. ............. 436/90 |
| 7,671,234 B2 | 3/2010 | Oftring et al. |
| 2003/0157247 A1 * | 8/2003 | Chikami et al. ............... 427/212 |
| 2004/0228978 A1 | 11/2004 | Jacob et al. |
| 2005/0020469 A1 * | 1/2005 | Rahse et al. ................... 510/444 |
| 2008/0045430 A1 * | 2/2008 | Witteler et al. ............... 510/218 |

(Continued)

FOREIGN PATENT DOCUMENTS

| DE | 101 62 781 A1 | 7/2003 |
| DE | 103 22 062 A1 | 12/2004 |

(Continued)

OTHER PUBLICATIONS

U.S. Appl. No. 61/253,908, filed Oct. 22, 2009, Mrzena, et al.

(Continued)

*Primary Examiner* — Lorna M Douyon
(74) *Attorney, Agent, or Firm* — Oblon, Spivak, McClelland, Maier & Neustadt, L.L.P.

(57) ABSTRACT

A process for producing granules containing one or more complexing agent salts of the general formula

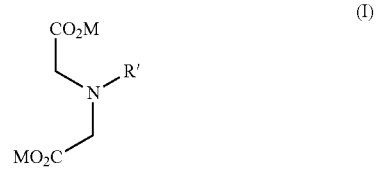

(I)

from an aqueous starting solution, containing the one or more complexing agent salts in a concentration of from 10 to 80% by weight, based on the total weight of the aqueous starting solution, in a jet apparatus.

16 Claims, 2 Drawing Sheets

(56) References Cited

U.S. PATENT DOCUMENTS

| | | | |
|---|---|---|---|
| 2010/0056817 A1* | 3/2010 | Meunier et al. | 556/112 |
| 2010/0152486 A1* | 6/2010 | Jacob et al. | 562/496 |
| 2012/0028874 A1* | 2/2012 | Fernandez Prieto et al. | 510/375 |

FOREIGN PATENT DOCUMENTS

| | | | |
|---|---|---|---|
| DE | 10 2005 037 630 A1 | | 2/2007 |
| EP | 0 845 456 A2 | | 6/1998 |
| WO | WO 94/29421 A1 | | 12/1994 |
| WO | WO 2006/120129 A1 | | 11/2006 |
| WO | WO2010/076291 A1 | * | 7/2010 |
| WO | WO 2011/045266 A1 | | 4/2011 |

OTHER PUBLICATIONS

U.S. Appl. No. 13/318,513, filed Nov. 2, 2011, Mrzena, et al.
U.S. Appl. No. 61/253,911, filed Oct. 22, 2009, Mrzena, et al.
U.S. Appl. No. 13/321,713, filed Nov. 21, 2011, Mrzena, et al.
A. Werner, Wirbelschicht-Sprühgranulation: Prozessoptimierung in der Strahlschicht [Fluidized-bed spray granulation: process optimization in the spouted bed], BASF SE and University of Stuttgart, Institute for Mechanical Process Engineering, Sep. 2009, pp. 1-58 (with English Abstract).
U.S. Appl. No. 13/501,390, filed Apr. 11, 2012, Mrzena, et al.

* cited by examiner

PROCESS FOR PRODUCING GRANULES COMPRISING ONE OR MORE COMPLEXING AGENT SALTS

CROSS-REFERENCES TO RELATED APPLICATIONS

This patent application claims the benefit of U.S. provisional patent application Ser. No. 61/386,590 filed Sep. 27, 2010 incorporated in its entirety herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF THE MATERIAL ON THE COMPACT DISC

Not Applicable

BACKGROUND OF THE INVENTION

The invention relates to a process for producing granules comprising one or more complexing agent salts of the general formula I

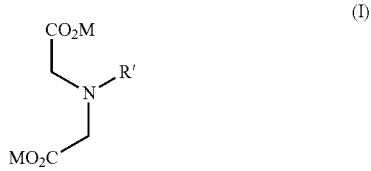

and to a use of the above granules.

FIELD OF THE INVENTION

The amino polyphosphonates, polycarboxylates or aminopolycarboxylates, such as ethylenediaminetetraacetic acid (EDTA), often used as complexing agents for example in detergents and cleaners, are biodegradable only to a small degree.

Description of the Related Art Including Information Disclosed Under 37 CFR 1.97 and 1.98

A cost-effective alternative is the glycine-N,N-diacetic acid derivatives, such as methylglycine-N,N-diacetic acid (MGDA) and salts thereof—e.g. the trialkali metal salts—which have advantageous toxicological properties and are readily biodegradable. The use of MGDA and of related glycine-N,N-diacetic acid derivatives in cleaners, and the syntheses thereof are described e.g. in WO-A 94/029421 or U.S. Pat. No. 5,849,950. For a cost-effective production of the glycine-N,N-diacetic acid derivatives, high requirements are placed on the yield of the individual synthesis steps and purity of the isolated intermediate products.

MGDA is produced in particular by reacting iminodiacetonitrile with acetaldehyde and hydrocyanic acid or alpha-alaninenitrile with formaldehyde and hydrocyanic acid and alkaline hydrolysis of the methylglycinediacetonitrile (MGDN) obtained as intermediate product with sodium hydroxide solution, giving the trisodium salt of MGDA. In order to achieve high MGDA yields and purities, MGDN is generally isolated as intermediate product and used as pure substance in the subsequent hydrolysis step.

A problem with the hydrolysis of alkylglycinenitrile-N,N-diacetonitriles is their thermal lability, especially in alkaline medium. As a result of the sterically demanding alkyl substitution, back-cleavage reactions are favored. Consequently, processes have been developed which as far as possible lead to low by-product forms of MGDA and its salts.

An improved process for producing low by-product salts of MGDA is described in WO 2006/120129. The more modern production processes generally lead to about 35 to 40% strength by weight aqueous solutions, from which the salts are then produced in flowable form.

One of the known work-up processes in the prior art is the conversion of such aqueous solutions in a spray tower. This produces predominantly amorphous powders with a residual moisture content in the order of magnitude of for example 5% by weight. Although higher residual moisture contents are conceivable, they are rather difficult to generate in a spray tower and are, moreover, also undesired because then upon subsequent storage by the consumer or during processing, clumping of the powders can arise. It is also known that granules do not have such disadvantages and can therefore be processed without problems. However, granule production requires an additional reworking step following powder production in the spray tower and is therefore relatively expensive. In this reworking step, additional moisture is fed to the powder from the spray tower, and granulation is carried out with heating and kneading at a residence time in the order of magnitude of one hour via a crystallization. Such a process is described for example in EP-A 08 45 456.

Complexing agent salts are often desired in coarsely granular form because this is associated with multiple advantages, in particular with improved flow behavior, easier handling and improved dosability.

A particularly advantageous process for producing coarsely particulate products is granulation in a special fluidized bed, the so-called spouted bed, also known as fluidized-bed spray granulation. The process is for example the subject of the thesis by A. Werner: Wirbelschicht-Sprühgranulation: Prozessoptimierung in der Strahlschicht [Fluidized-bed spray granulation: process optimization in the spouted bed], September 2009, BASF SE and University of Stuttgart, Institute for mechanical process engineering.

The corresponding apparatuses are often referred to in the specialist literature and patent literature as spouted-bed apparatuses and are described for example in DE 10 2005 037 630, DE 10 162 781 or DE 103 22 062.

However, in these apparatuses no clearly visible boundary is formed between the fluidizing material and the gas space lying above, in contrast to a classic fluidized bed, meaning that in the present case the term jet apparatus is used for this.

BRIEF SUMMARY OF THE INVENTION

It was an object of the invention to provide a process for producing granules of one or more complexing agent salts with improved space-time yield and improved product quality, in particular with more compact, more uniform particle form and with parameters derived therefrom, in particular higher bulk density, lower susceptibility to breakage and better flowability.

BRIEF DESCRIPTION OF THE SEVERAL VIEWS OF THE DRAWINGS

FIG. 1 is a scanning electron micrograph of round compact granules obtained by spray granulating a 40% strength aqueous Trilon M® solution.

FIG. 2 is a scanning electron micrograph of irregularly shaped granules obtained by spray-granulating a 40% strength aqueous Trilon M® solution in a fluidized bed.

DETAILED DESCRIPTION OF THE INVENTION

Figure 1:
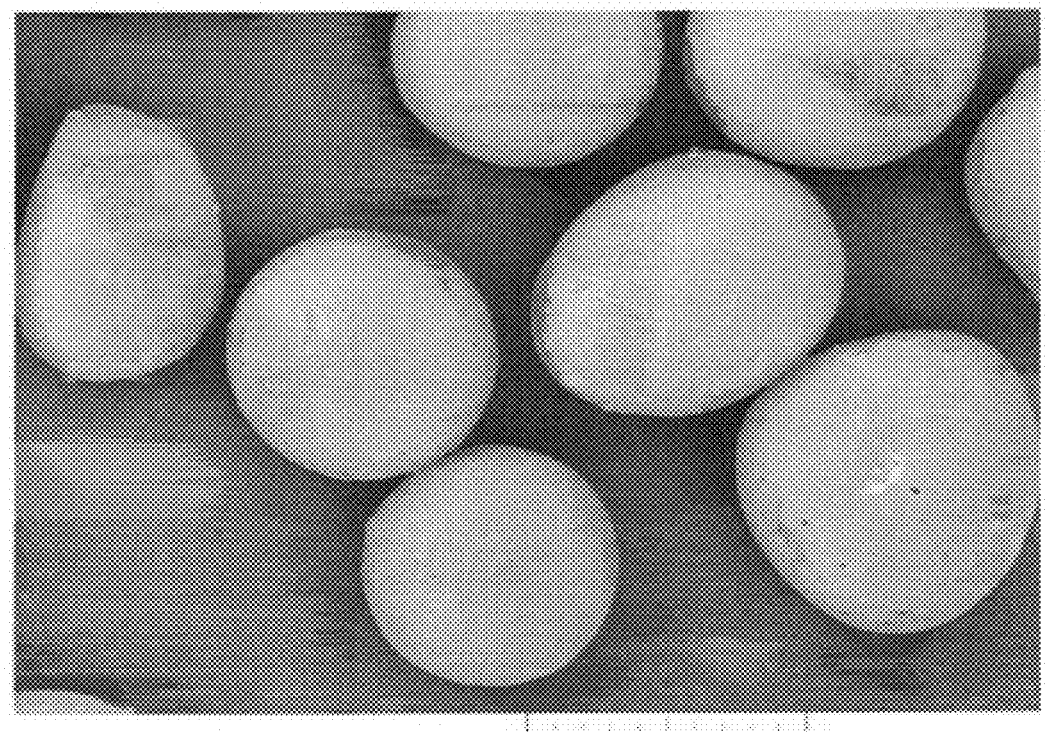
FIG. 1.

The object is achieved by a process for producing granules comprising one or more complexing agent salts of the general formula

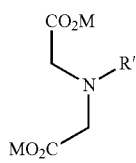
(I)

in which
R' is hydrogen or one of the groups

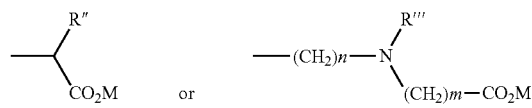

where
R" is hydrogen, a $C_1$-$C_{12}$-alkyl radical or a —$(CH_2)_q$—COOM radical where q=1 to 5
n and m are in each case an integer from 0 to 5 and
R'" is hydrogen or a $C_1$-$C_{12}$-alkyl radical or a $C_2$-$C_{12}$-alkenyl radical, which may be additionally substituted with up to 5 hydroxyl groups,
or is one of the groups

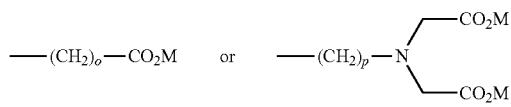

in which o and p are in each case an integer from 0 to 5, and M, independently of the others, is hydrogen, alkali metal, alkaline earth metal, ammonium or substituted ammonium in the corresponding stoichiometric amounts,
from an aqueous starting solution comprising the one or more complexing agent salts in a concentration of from 10 to 80% by weight, based on the total weight of the aqueous starting solution,
in a jet apparatus, in which a gaseous driving jet positioned centrally and directed from bottom to top, or one or more gaseous driving jets positioned in the region of the central axis of the jet apparatus induce an internal loop motion, with formation of a jet zone, joined to the upper end of which is a fountain zone, which merges into a return zone in the wall region of the jet apparatus, which return zone in turn, in its lower region, merges into the jet zone, where the aqueous starting solution is sprayed into the one or more gaseous driving jets and in so doing is dried to give the granules, which are discharged from the jet apparatus.

The defined flow profile in the jet apparatus, with internal loop motion, ensures that the granule particles that are forming regularly pass by one or more nozzles, via which the aqueous starting solution is sprayed in, meaning that they are sprayed regularly, in clearly defined time intervals, resulting in the regular growth of superimposed layers in the manner of superimposed onion skins, and consequently grow to give very uniform particles. The granules obtained here have excellent product properties, in particular very high, defined bulk density, in the range between 650 and 1000 $kg/m^3$, in particular between 760 and 920 $kg/m^3$, and also a defined residual moisture required for the intended use, in the range from ca. 6 to 14% by weight of water, in particular 11 to 13% by weight of water.

Granules of the above complexing agent salts with a preferred residual moisture of >8% by weight, in particular >12% by weight, often stick in standard fluidized-bed apparatuses, but can be produced without problems in the jet apparatuses used according to the invention.

For this purpose, the starting material is an aqueous solution of one or more complexing agent salts with a concentration in the range from 10 to 80% by weight, based on the total weight of the aqueous solution. The aqueous starting solution can preferably be prewarmed up to below the boiling point of same.

The one or more complexing agent salts correspond to the general formula

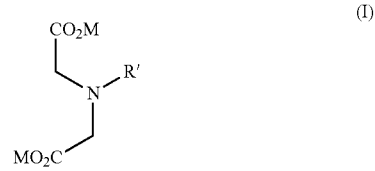
(I)

in which
R' is hydrogen or one of the groups

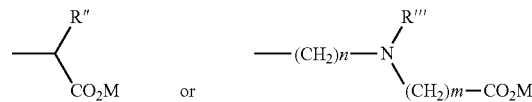

where
R" is hydrogen, a $C_1$-$C_{12}$-alkyl radical or a —$(CH_2)_q$—COOM radical where q=1 to 5
n and m are in each case an integer from 0 to 5 and
R'" is hydrogen or a $C_1$-$C_{12}$-alkyl radical or a $C_2$-$C_{12}$-alkenyl radical, which may be additionally substituted with up to 5 hydroxyl groups,
or is one of the groups

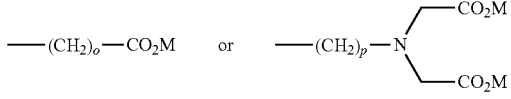

in which o and p are in each case an integer from 0 to 5, and
M, independently of the others, is hydrogen, alkali metal, alkaline earth metal, ammonium or substituted ammonium in the corresponding stoichiometric amounts.

Preferably, these are derivatives of glycine-N,N-diacetic acid or derivatives of glutamine-N,N-diacetic acid. Preference is also given to derivatives of ethylenediamine-triacetic acid or of nitrilotriacetic acid.

Particularly preferred derivatives of glycine-N,N-diacetic acid are alkali metal salts of methylglycine-N,N-diacetic acid, referred to below as MGDA.

The aqueous starting solution is sucked into the driving jet of a jet apparatus, sprayed by the driving jet and dried, giving granules which are discharged in the upper region of the jet apparatus.

According to the definition in the thesis by A. Werner cited above in the Introduction to the description, fluidized-bed spray granulation is a shaping process for producing coarsely granular, monodisperse and virtually round particles having particle sizes in the range between 0.3 mm and 30 mm, which are in the present case referred to as granules, starting from solutions, suspensions or melts.

The fluidized-bed spray granulation is carried out in a so-called spouted bed which is a specific variant of a fluidized bed: In a standard fluidized bed, particles are fluidized by collectively blowing gas into a particle from below via a perforated base with a large number of perforations (openings), whereupon the particles are fluidized.

By contrast, in a so-called spouted bed, the fluidizing takes place via one or more openings in the base of the jet apparatus, via which one or more driving jets are sprayed in. The one or more driving jets induce an internal, ordered loop motion, which can also be referred to as circular motion or cylindrical motion, and which comprises essentially three fluidization states or zones, namely a jet zone, a fountain zone and a return zone. In a first zone or jet zone, the acceleration of the solid particles takes place, under the action of the driving jet guided in a defined manner from bottom to top, during which the particles move within this zone in the flow direction of the driving jet. Accordingly, a flow directed vertically upwards prevails in the jet zone. In a subsequent second zone or fountain zone, the solid particles change their direction of flow; a cross flow prevails. Finally, the particles enter a third zone or return zone in the wall region of the jet apparatus, where they have a motion directed downwards until they in turn arrive in the region of the driving jet guided from bottom to top and are in turn entrained by the driving jet in the first zone, the jet zone. In the return zone, the particles are typically moving under the influence of gravity.

As jet apparatus, preference is given to using a cylindrical apparatus which conically tapers in the lower region of same by spraying in a central driving jet from below.

In a further preferred embodiment, a driving jet apparatus with rectangular cross section can be used which tapers in a lower section and in which, in the region of the central axis of same, one or more driving jets are positioned from bottom to top. Such an apparatus is described for example in DE 103 22 062.

Preferably, the one or more gaseous driving jets are formed from a gas which is under a positive pressure in the range from 20 mbar to 1 bar above the pressure in the jet apparatus, which decompresses via an opening in the jet apparatus and in so doing forms the gaseous driving jet. The driving jet is formed from a gas stream which is preferably an inert gas, in particular air. In a particularly preferred embodiment of the present process, crystalline fine dust with an average particle diameter in the range from about 1 to 100 µm, preferably from about 1 to 20 µm, is added to the jet apparatus separately from the aqueous starting solution at a position in the jet apparatus which is different from the position at which the aqueous starting solution is sprayed in.

In one advantageous embodiment, the crystalline fine dust comprises the same complexing agent salt(s) as are present in the aqueous starting solution, or one or more complexing agent salts different therefrom.

In a further preferred embodiment, the aqueous starting solution is premixed with crystalline fine dust with an average particle diameter in the range from about 1 to 100 µm, preferably from about 1 to 20 µm, giving a suspension, sprayed in in the lower region of the jet apparatus and sucked in by the driving jet.

It is also possible to use cascaded jet apparatuses, i.e. two or more apparatuses connected in series, configured as described above.

Preferably, the gas stream forming the driving jet has a temperature in the range between 80 and 450° C., further preferably between 120 and 240° C.

The temperature in the jet zone, in the fountain zone and in the return zone is preferably in the range between 70 and 150° C.

The residence time in the jet apparatus is preferably between 1 minute and 1 hour, in particular between 10 minutes and 40 minutes.

The invention also provides formulations comprising the granules produced by the process described above, or aqueous solutions thereof, as complexing agent for alkaline earth metal ions and heavy metal ions in the amounts customary for this purpose, besides other customary constituents of such formulations.

These are preferably detergent and cleaner formulations.

The invention also provides the use of the granules produced by the process described above for producing pressed agglomerates.

The pressed agglomerates are preferably used in solid cleaners which are intended in particular for use in dishwashers.

The invention is illustrated below by reference to working examples.

EXAMPLE

According to the Invention

In a jet apparatus of the type ProCell 5 from Glatt, a 40% strength aqueous Trilon M® solution (trisodium salt of methylglycine-N,N-diacetic acid) was spray-granulated. The jet apparatus was operated with a volume stream of 180 Nm$^3$/h of air with an entry temperature of 180° C. as driving jet. In the lower region of the jet apparatus, 9.5 kg/h of the aqueous solution were sprayed in by means of a two-material nozzle. As atomizing gas, compressed air at 8 bar was used here. The temperature in the jet apparatus was 80° C.

Under these conditions, round, compact granules were obtained corresponding to the scanning electron micrographs shown in FIG. 1. The particle size was in the range from 0.4 to 2 mm and the bulk density was 900 kg/m$^3$.

COMPARATIVE EXAMPLE

For the comparison, the same 40% strength aqueous Trilon M® solution was spray-granulated, but in a fluidized bed. For this, a fluidized-bed apparatus with a diameter of 300 mm from BASF SE was used.

The granulation fluidized bed was operated with a volume stream of 205 Nm$^3$/h of air with an entry temperature of 160° C. In the lower region of the granulation fluidized bed, 5.3 kg/h of the aqueous solution were sprayed in using a two-material nozzle. The atomization gas used here was compressed air at 5 bar. The temperature in the granulation fluidized bed was 100° C.

Figure 2:
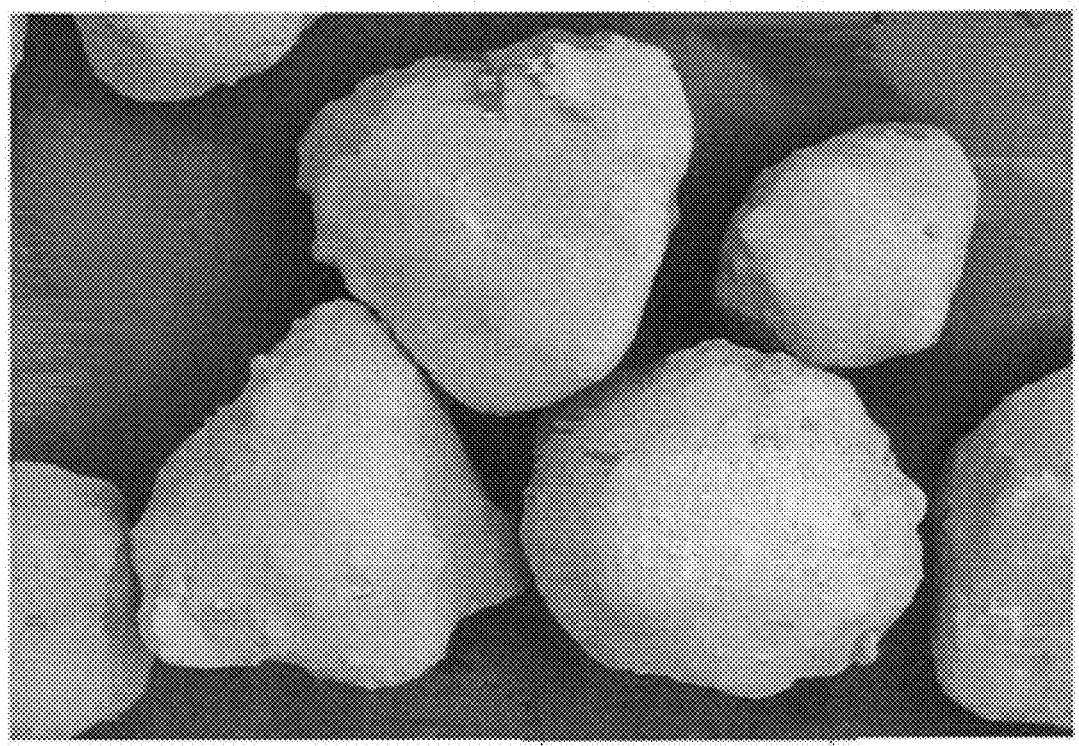
FIG. 2.

Under these conditions, irregularly shaped granules were obtained corresponding to the scanning electron micrograph shown in FIG. 2. The particle size was in the range from 0.4 to 2 mm and the bulk density was 750 kg/m$^3$.

The experiments thus demonstrate that a significantly more uniform particle form and a clearly increased bulk density of the granules are achieved by the process according to the invention.

The invention claimed is:

1. A process for producing granules, the process comprising spraying an aqueous starting solution into one or more gaseous driving jets in a jet apparatus, drying the aqueous starting solution to obtain round compact granules, and discharging the granules from the jet apparatus, wherein:
the granules comprise one or more complexing agent salts of formula (I):

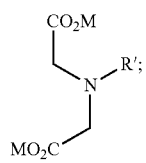
(I)

R' represents hydrogen or one of the groups:

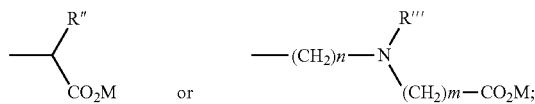

R" represents hydrogen, a $C_1$-$C_{12}$-alkyl radical, or a —(CH$_2$)$_q$—COOM radical;
q represents 1 to 5;
n and m independently represent an integer from 0 to 5;
R''' represents hydrogen, or a $C_1$-$C_{12}$-alkyl radical or a $C_2$-$C_{12}$-alkenyl radical, which are optionally substituted with up to 5 hydroxyl groups, or is one of the groups:

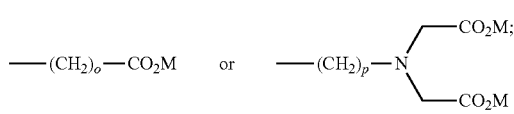

o and p independently represent an integer from 0 to 5;
M independently represents hydrogen, an alkali metal, an alkaline earth metal, or an ammonium or a substituted ammonium in corresponding stoichiometric amounts;
the aqueous starting solution comprises the one or more complexing agent salts in a concentration of from 10 to 80% by weight, based on a total weight of the aqueous starting solution;
in the jet apparatus,
a gaseous driving jet is positioned centrally and directed from bottom to top, or one or more gaseous driving jets are positioned in a region of the central axis of the jet apparatus, to induce an internal loop motion, with formation of a jet zone, a fountain zone is present in an upper end of the jet apparatus,
the fountain zone merges into a return zone in a wall region of the jet apparatus, and
the return zone, in its lower region, merges into the jet zone, where the aqueous starting solution is sprayed into the one or more gaseous driving jets;
the temperature in the jet zone, the fountain zone, and in the return zone is in a range between 70 and 150° C.; and
the round compact granules have particle sizes in the range of between 0.3 and 30 mm and a bulk density ranging from 900 kg/m$^3$ to 1000 kg/m$^3$.

2. The process according to claim 1, wherein the jet apparatus is a cylindrical apparatus which is conically tapered in its lower region, and into which a central gaseous driving jet is sprayed.

3. The process according to claim 1, wherein the jet apparatus has a rectangular cross section which tapers in its lower section, and comprises one or more gaseous driving jets which are positioned in a region of the central axis of the jet apparatus and are directed from bottom to top.

4. The process according to claim 1, wherein the one or more gaseous driving jets are formed from a gas which is under a positive pressure in a range from 20 mbar to 1 bar above a pressure in the jet apparatus, such that the gas decompresses through at least one opening in the jet apparatus to form the one or more gaseous driving jets.

5. The process according to claim 1, wherein the aqueous starting solution is sprayed through one or more single-material or two-material nozzles into the lower region of the jet apparatus.

6. The process according to claim 1, further comprising adding a crystalline fine dust, with an average particle diameter in a range from about 1 to 100 μm, to the jet apparatus, separately from the aqueous starting solution, at a position in the jet apparatus which is different from a spraying position of the aqueous starting solution.

7. The process according to claim 6, wherein the crystalline fine dust comprises the one or more complexing agent salts or one or more different complexing agent salts.

8. The process according to claim 6, wherein the crystalline fine dust has an average particle diameter in a range from about 1 to 20 μm.

9. The process according to claim 1, further comprising premixing the aqueous starting solution and a crystalline fine dust, having an average particle diameter in the range from about 1 to 100 μm, to give a suspension, which is sprayed into the lower region of the jet apparatus and sucked in by the one or more gaseous driving jets.

10. The process according to claim 9, wherein the crystalline fine dust has an average particle diameter in a range from about 1 to 20 μm.

11. The process according to claim 1, wherein a gas stream forming the one or more driving jets has a temperature in a range between 80 and 450° C.

12. The process according to claim 11, wherein the gas stream forming the driving jet has a temperature in a range between 120 and 240° C.

13. The process according to claim 1, wherein an average residence time of the granules in the jet apparatus is between 1 minute and 1 hour.

14. The process according to claim 13, wherein the average residence time of the granules in the jet apparatus is between 10 minutes and 40 minutes.

15. The process of claim 1, wherein the granules produced have particle sizes in the range from 0.4 to 2 mm.

16. The process of claim 1, wherein the granules produced have a residual moisture content ranging from 6 to 14% by weight of water.

\* \* \* \* \*